US007183438B2

(12) United States Patent
Gerlach et al.

(10) Patent No.: US 7,183,438 B2
(45) Date of Patent: Feb. 27, 2007

(54) CATALYSTS AND METHOD FOR THE PRODUCTION OF AMINES

(75) Inventors: Till Gerlach, Ludwigshafen (DE); Frank Funke, Mannheim (DE); Johann-Peter Melder, Böhl-Iggelheim (DE); Stefan Iselborn, Ludwigshafen (DE); Martin Rudloff, Weisenheim (DE); Michael Hüllmann, Bensheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 275 days.

(21) Appl. No.: 10/507,602

(22) PCT Filed: Mar. 7, 2003

(86) PCT No.: PCT/EP03/02335

§ 371 (c)(1),
(2), (4) Date: Sep. 14, 2004

(87) PCT Pub. No.: WO03/076386

PCT Pub. Date: Sep. 18, 2003

(65) Prior Publication Data

US 2005/0107637 A1    May 19, 2005

(30) Foreign Application Priority Data

Mar. 14, 2002 (DE) ................................ 102 11 101

(51) Int. Cl.
*C07C 209/16* (2006.01)
*C07C 209/18* (2006.01)
*C07C 209/29* (2006.01)
*B01J 23/40* (2006.01)
*B01J 23/42* (2006.01)

(52) U.S. Cl. ...................... 564/397; 564/398; 564/401; 564/402; 564/403; 564/472; 564/473; 564/480; 502/326

(58) Field of Classification Search ..................... None
See application file for complete search history.

(56) References Cited

U.S. PATENT DOCUMENTS

| 5,002,922 | A | 3/1991 | Irgang et al. |
| 5,530,127 | A | 6/1996 | Reif et al. |
| 5,608,113 | A | 3/1997 | Becker et al. |
| 6,057,442 | A | 5/2000 | Wulff-Doring et al. |
| 6,417,353 | B1 | 7/2002 | Funke et al. |
| 6,525,222 | B2 | 2/2003 | Nouwen et al. |

FOREIGN PATENT DOCUMENTS

| DE | 101 42635 | 3/2003 |
| EP | 017 651 | 10/1982 |
| EP | 382 049 | 8/1990 |
| EP | 514 692 | 11/1992 |
| EP | 696 572 | 2/1996 |
| EP | 697 395 | 2/1996 |
| EP | 905 122 | 3/1999 |
| EP | 963 975 | 12/1999 |
| EP | 1 103 106 | 9/2000 |
| EP | 1 106 600 | 6/2001 |

*Primary Examiner*—Brian Davis
(74) *Attorney, Agent, or Firm*—Novak Druce & Quigg LLP

(57) ABSTRACT

Disclosed are catalysts, the catalytically active mass of which contains 22 to 40 percent by weight of oxygen-containing compounds of zirconium, calculated as $ZrO_2$, 1 to 30 percent by weight of oxygen-containing compounds of copper, calculated as CuO, 15 to 50 percent by weight of oxygen-containing compounds of nickel, calculated as NiO, the molar ratio between nickel and copper being greater than 1, 15 to 50 percent by weight of oxygen-containing compounds of cobalt, calculated as CoO, and less than 1 percent by weight of an alkali metal, calculated as alkali metal oxide, prior to being treated with hydrogen. Also disclosed is a method for the production of amines by reacting primary and secondary alcohols, aldehydes, or ketones with hydrogen and nitrogen compounds selected from the group ammonia, primary and secondary amines, in the presence of said catalysts at an elevated temperature and an elevated pressure.

9 Claims, 2 Drawing Sheets

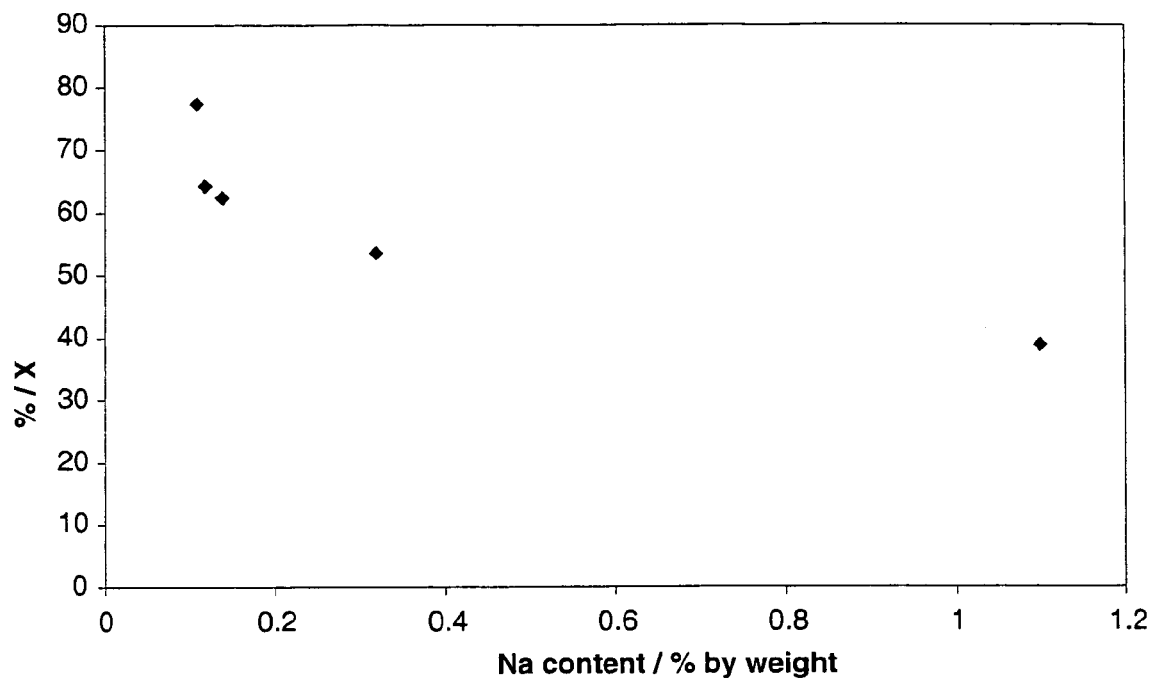
Figure 1: Conversion (X in %) of ethylene glycol in the reductive amination to form aminodiglycol and morpholine at a reaction temperature of 180°C as a function of the sodium content of the catalysts (catalysts A1 to A5)

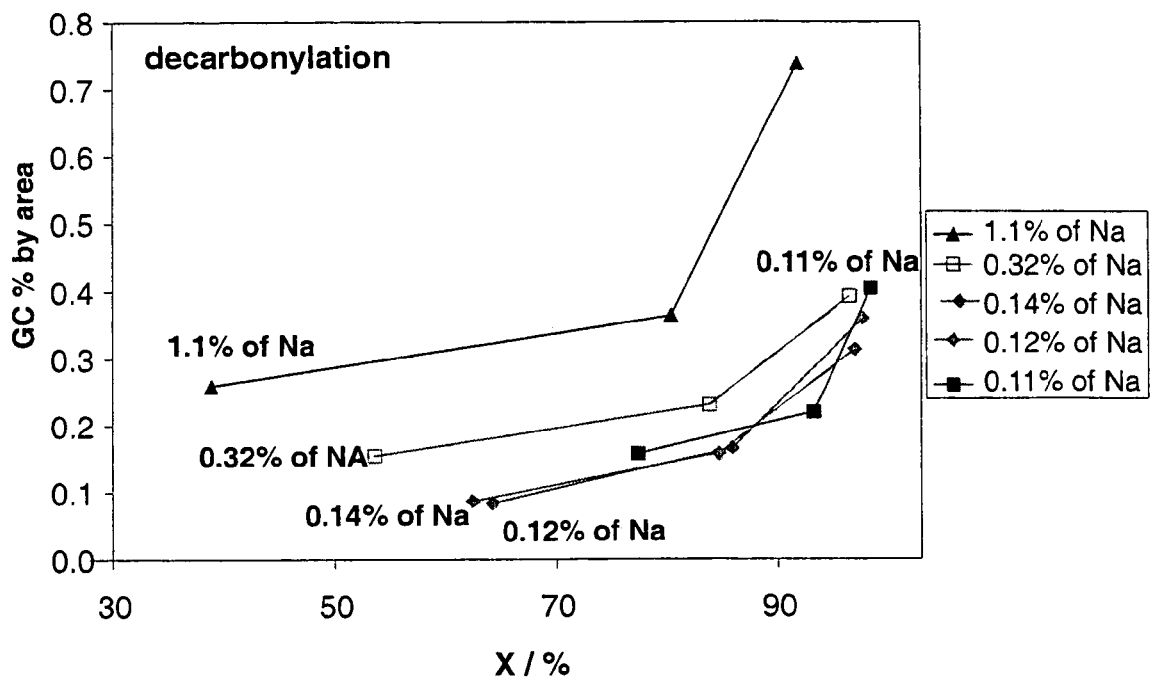
Figure 2: Selectivity (in GC % by area) to the (undesirable) products of decarbonylation (2-methoxyethanol und 2-methoxyethylamine) as a function of the diethylene glycol conversion (X in %) for the catalysts A1 to A5

CATALYSTS AND METHOD FOR THE PRODUCTION OF AMINES

This application is a 371 of PCT/EP/03/02335 filed Mar. 7, 2003.

The present invention relates to novel catalysts which comprise zirconium, copper, cobalt and nickel and are low in alkali metals or free of alkali metals and also to the use of these catalysts in a process for preparing amines by reacting primary or secondary alcohols, aldehydes or ketones with hydrogen and nitrogen compounds selected from the group consisting of ammonia and primary and secondary amines at elevated temperature and superatmospheric pressure.

EP-A1-382 049 (BASF AG) discloses catalysts comprising oxygen-containing zirconium, copper, cobalt and nickel compounds and processes for the hydrogenative amination of alcohols. The preferred zirconium oxide content of these catalysts is from 70 to 80% by weight (loc. cit.: page 2, last paragraph; page 3, 3rd paragraph; examples). Although these catalysts display a good activity and selectivity, they have operating lives which are in need of improvement.

EP-A2-514 692 (BASF AG) discloses catalysts comprising copper oxide, nickel oxide and/or cobalt oxide, zirconium oxide and/or aluminum oxide for the catalytic amination of alcohols in the gas phase by means of ammonia or primary amines and hydrogen.

This patent application teaches that in these catalysts the atomic ratio of nickel to copper has to be from 0.1 to 1.0, preferably from 0.2 to 0.5 (cf. loc. cit.: example 1), since otherwise there is increased formation of yield-reducing by-products in the amination of alcohols (loc. cit.: examples 6 and 12). As support, preference is given to using aluminum oxide (loc. cit.: examples 1 to 5 and 7 to 11).

EP-A1-696 572 and EP-A-697 395 (both BASF AG) disclose catalysts comprising nickel oxide, copper oxide, zirconium oxide and molybdenum oxide for the catalytic amination of alcohols by means of nitrogen compounds and hydrogen. Although these catalysts give high conversions, there can be formation of by-products (e.g. ethylamine) which themselves or in the form of their downstream products interfere in the work-up.

EP-A2-905 122 (BASF AG) describes a process for preparing amines from alcohols and nitrogen compounds using a catalyst whose catalytically active composition comprises oxygen-containing compounds of zirconium, copper and nickel, and no oxygen-containing compounds of cobalt or molybdenum.

EP-A-1 035 106 (BASF AG) relates to the use of catalysts comprising oxygen-containing compounds of zirconium, copper and nickel for preparing amines by aminative hydrogenation of aldehydes or ketones.

EP-A1-963 975 and EP-A2-1 106 600 (both BASF AG) describe processes for preparing amines from alcohols or aldehydes or ketones and nitrogen compounds using a catalyst whose catalytically active composition comprises 22–40% by weight (or 22–45% by weight) of oxygen-containing compounds of zirconium, 1–30% by weight of oxygen-containing compounds of copper, 15–50% by weight (or 5–50% by weight) of oxygen-containing compounds of nickel and 15–50% by weight (or 5–50% by weight) of oxygen-containing compounds of cobalt.

When the very active catalysts of EP-A1–963 975 and EP-A2–1 106 600 are used, increased decarbonylation of any carbonyl function formed as an intermediate can occur at elevated temperatures. The formation of methane by hydrogenation of carbon monoxide (CO) leads, owing to the large quantity of heat of hydrogenation liberated, to the risk of a "runaway" reaction, i.e. an uncontrolled temperature rise in the reactor. If CO is trapped by reaction with amines, methyl-containing secondary components are formed. For example, in the amination of diethylene glycol, there is increased formation of undesirable methoxyethanol or methoxyethylamine.

Scheme:

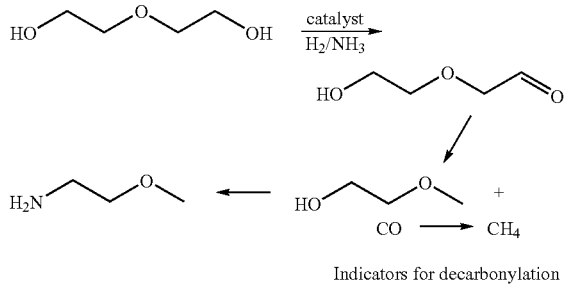

Indicators for decarbonylation

As reaction mechanism of the amination of primary or secondary alcohols, it is assumed that the alcohol is initially dehydrogenated at a metal center to form the corresponding aldehyde. Here, the copper is presumably of particular importance as dehydrogenation component. If aldehydes are used for the amination, this step does not occur.

The aldehyde formed or used can be aminated by reaction with ammonia or primary or secondary amine with elimination of water and subsequent hydrogenation. This condensation of the aldehyde with the abovementioned nitrogen compound is presumably catalyzed by acidic centers on the catalyst. In an undesirable secondary reaction, however, the aldehyde can also be decarbonylated, i.e. the aldehyde function is split off as CO. Decarbonylation or methanization presumably takes place at a metallic center. The CO is hydrogenated to methane over the hydrogenation catalyst, so that the formation of methane indicates the extent of decarbonylation. The decarbonylation forms the above-mentioned undesirable by-products such as methoxyethanol or methoxyethylamine.

The desired condensation of the aldehyde with ammonia or primary or secondary amine and the undesirable decarbonylation of the aldehyde are parallel reactions of which the desired condensation is acid-catalyzed while the undesirable decarbonylation is catalyzed by metallic centers.

It is an object of the present invention to improve the economics of previous processes for the hydrogenative amination of aldehydes or ketones and the amination of alcohols and to remedy the disadvantages of the prior art, in particular the abovementioned disadvantages. Catalysts which can be produced industrially in a simple manner and allow the above-mentioned aminations to be carried out with high conversion, high yield, selectivity and catalyst operating life and at the same time have a high mechanical stability of the shaped catalyst body and result in a low risk of a runaway reaction are to be found. The catalysts should accordingly have a high activity and a high chemical and mechanical stability under the reaction conditions.

We have found that this object is achieved by catalysts whose catalytically active composition prior to treatment with hydrogen comprises from 22 to 40% by weight of oxygen-containing compounds of zirconium, calculated as $ZrO_2$, from 1 to 30% by weight of oxygen-containing compounds of copper, calculated as CuO, from 15 to 50% by weight of oxygen-containing compounds of nickel, calculated as NiO, with the molar ratio of nickel to copper being greater than 1, from 15 to 50% by weight of oxygen-containing compounds of cobalt, calculated as CoO, and less than 1% by weight of alkali metal (M), calculated as alkali metal oxide ($M_2O$), and also their advantageous use for preparing amines by reacting primary or secondary alcohols, aldehydes or ketones with hydrogen and nitrogen compounds selected from the group consisting of ammonia and primary and secondary amines at elevated temperature and superatmospheric pressure.

Furthermore, we have found an improved process for preparing amines by reacting primary or secondary alcohols, aldehydes or ketones with hydrogen and nitrogen compounds selected from the group consisting of ammonia, primary and secondary amines at elevated temperature and superatmospheric pressure in the presence of a catalyst according to the present invention as defined above. According to the present invention, it was recognized that the activity of the catalyst in the amination of primary or secondary alcohols, aldehydes or ketones in the presence of $H_2$, e.g. the amination of diethylene glycol by means of ammonia to form aminodiglycol and morpholine, increases with decreasing alkali metal content, e.g. sodium content, of the zirconium-copper-nickel-cobalt catalysts.

At the same time, the extent of the undesirable decarbonylation reaction decreases.

A particularly low tendency for the undesirable decarbonylation to occur is observed in the case of catalysts containing less than 0.5% by weight, in particular less than 0.35% by weight, very particularly preferably less than 0.2% by weight, of alkali metal, in each case calculated as alkali metal oxide.

The alkali metal content can be influenced, for example, by the time for which the filter cake obtained in the preparation of the catalyst is washed, with a prolonged washing time leading to a reduced alkali metal content.

BRIEF DESCRIPTION OF THE DRAWING(S)

FIG. 1 illustrates the productivity of exemplary catalysts containing varying amounts of sodium as a function of the sodium content FIG. 2 illustrates the selectivity of exemplary catalysts containing varying amounts of sodium as a function of the conversion rate In general, the process of the present invention is preferably carried out using catalysts which consist entirely of catalytically active composition and, if desired, a shaping aid (e.g. graphite or stearic acid) if the catalyst is used as shaped bodies, i.e. contain no further catalytically inactive accompanying substances.

The catalytically active composition can be introduced into the reaction vessel as powder after milling or as crushed material, but is preferably introduced into the reactor as shaped catalyst bodies, for example as pellets, spheres, rings, extrudates, after milling, mixing with shaping aids, shaping and heat treatment.

The indicated concentrations (in % by weight) of the components of the catalyst are in each case based, unless indicated otherwise, on the catalytically active composition of the catalyst prior to treatment with hydrogen.

The catalytically active composition of the catalyst is defined as the sum of the catalytically active constituents and, prior to treatment with hydrogen, consists essentially of the oxygen-containing compounds of zirconium, copper, nickel and cobalt.

The sum of the abovementioned catalytically active constituents, calculated as $ZrO_2$, CuO, NiO and CoO, in the catalytically active composition prior to treatment with hydrogen is usually from 70 to 100% by weight, preferably from 80 to 100% by weight, particularly preferably from 90 to 100% by weight, in particular from 95 to 100% by weight, very particularly preferably from >99 to 100% by weight.

The oxygen-containing compounds of nickel, cobalt and copper, in each case calculated as NiO, CoO and CuO, are generally present in a total amount of from 31 to 78% by weight, preferably from 44 to 75% by weight, particularly preferably from 55 to 75% by weight, in the catalytically active composition (prior to treatment with hydrogen), with the molar ratio of nickel to copper being greater than 1.

The content of alkali metal M, calculated as alkali metal oxide $M_2O$, in the catalytically active composition of the catalysts of the present invention prior to treatment with hydrogen is less than 1% by weight, preferably less than 0.5% by weight, particularly preferably less than 0.35% by weight, in particular less than 0.2% by weight.

The alkali metals M are Li, Na, K, Rb and/or Cs, in particular Na and/or K, very particularly preferably Na.

The catalytically active composition of the catalysts of the present invention prior to treatment with hydrogen comprises from 22 to 40% by weight, preferably from 25 to 40% by weight, particularly preferably from 25 to 35% by weight, of oxygen-containing compounds of zirconium, calculated as $ZrO_2$, from 1 to 30% by weight, preferably from 2 to 25% by weight, particularly preferably from 5 to 15% by weight, of oxygen-containing compounds of copper, calculated as CuO, from 15 to 50% by weight, preferably from 21 to 45% by weight, particularly preferably from 25 to 40% by weight, of oxygen-containing compounds of nickel, calculated as NiO, with the molar ratio of nickel to copper being greater than 1, preferably greater than 1.2, particularly preferably from 1.8 to 8.5, from 15 to 50% by weight, preferably from 21 to 45% by weight, particularly preferably from 25 to 40% by weight, of oxygen-containing compounds of cobalt, calculated as CoO, and less than 1% by weight, preferably less than 0.5% by weight, particularly preferably less than 0.35% by weight, in particular less than 0.2% by weight, of alkali metal M, calculated as alkali metal oxide $M_2O$.

A variety of methods are possible for preparing the catalysts. They are obtainable, for example, by peptization of pulverulent mixtures of the hydroxides, carbonates, oxides and/or other salts of the components with water and subsequent extrusion and heat treatment of the mass obtained in this way.

However, precipitation methods are generally employed for preparing the catalysts of the present invention. Thus, for example, they can be obtained by coprecipitation of the nickel, cobalt and copper components from an aqueous salt solution in which these elements are present by means of bases in the presence of a slurry of a sparingly soluble, oxygen-containing zirconium compound and subsequent washing, drying and calcination of the precipitate obtained. As sparingly soluble, oxygen-containing zirconium compounds, it is possible to use, for example, zirconium dioxide, zirconium oxide hydrate, zirconium phosphates, borates and silicates. The slurries of the sparingly soluble zirconium compounds can be produced by suspending fine powders of these compounds in water with vigorous stirring. The slurries are advantageously obtained by precipitation of the sparingly soluble zirconium compounds from aqueous zirconium salt solutions by means of bases.

The catalysts of the present invention are preferably prepared by coprecipitation of all their components. For this purpose, it is advantageous to add an aqueous base, for example sodium carbonate, sodium hydroxide, potassium carbonate or potassium hydroxide, to a hot aqueous salt solution comprising the catalyst components while stirring until the precipitation is complete. It is also possible to employ bases which are free of alkali metal, e.g. ammonia, ammonium carbonate, ammonium hydrogen carbonate, ammonium carbamate, ammonium oxalate, ammonium malonate, urotropin, urea, etc. The type of salts used is generally not critical: since the water solubility of the salts is of primary importance in this procedure, a criterion is a good solubility in water to allow the preparation of these relatively highly concentrated salt solutions. It will be self evident to a person skilled in the art that the salts chosen for the individual components should be salts containing anions which do not lead to interference, whether by causing undesirable precipitates or by hindering or preventing precipitation due to complex formation.

The precipitates obtained in these precipitation reactions are generally chemically nonuniform and comprise, inter alia, mixtures of the oxides, hydrated oxides, hydroxides, carbonates and insoluble and basic salts of the metals used. To improve the filterability of the precipitates, it may be found to be useful for them to be aged, i.e. for them to be left to stand for some time after the precipitation, if appropriate while hot or while passing air through them.

The precipitates obtained after these precipitation processes are processed further in a customary fashion to give the catalysts of the present invention. The precipitates are firstly washed. The alkali metal content which has been introduced by any (mineral) base used as precipitant can be influenced by the duration of the washing procedure and by the temperature and amount of the washing water. In general, an increase in the washing time or an increase in the temperature of the washing water results in a decrease in the alkali metal content. After washing, the precipitated material is generally dried at from 80 to 200° C., preferably from 100 to 150° C., and then calcined. The calcination is generally carried out at from 300 to 800° C., preferably from 400 to 600° C., in particular from 450 to 550° C.

After the calcination, the catalyst is advantageously conditioned, either by milling to a particular particle size or by firstly milling it, mixing it with shaping aids such as graphite or stearic acid, pressing it by means of a tableting press to give shaped bodies and heat treating these. The heat treatment temperatures generally correspond to the calcination temperatures.

In the catalysts prepared in this way, the catalytically active metals are present in the form of a mixture of their oxygen-containing compounds, i.e. in particular as oxides and mixed oxides.

The preparation of the zirconium-copper-nickel-cobalt catalysts of the present invention which are low in alkali metal or free of alkali metal can also be carried out by methods analogous to those described in the earlier German patent application No. 10142635.6 of Aug. 31, 2001, which is hereby expressly incorporated by reference.

After they have been prepared, the catalysts can be stored as such. Before use as catalysts for the hydrogenative amination of alcohols, aldehydes or ketones, they are usually prereduced by treatment with hydrogen. However, they can also be used without prereduction, in which case they are then reduced under the conditions of the hydrogenative amination by the hydrogen present in the reactor. To prereduce the catalysts, they are generally firstly exposed to a nitrogen/hydrogen atmosphere at from 150 to 200° C. for from 12 to 20 hours and subsequently treated in a hydrogen atmosphere at from 200 to 400° C. for up to about 24 hours. In this prereduction, part of the oxygen-containing metal compounds present in the catalysts are reduced to the corresponding metals, so that these are present together with the various oxygen compounds in the active form of the catalyst.

A further advantage of the catalysts of the present invention is their mechanical stability, i.e. their hardness. The mechanical stability can be determined by measurement of the lateral compressive strength. For this purpose, the shaped catalyst body, e.g. the catalyst pellet, is subjected to an increasing force between two parallel plates, with this force being able to be applied, for example, to the cylindrical surface of catalyst pellets until fracture of the shaped catalyst body occurs. The force recorded when fracture of the shaped catalyst body occurs is the lateral compressive strength.

Amines of the Formula I

where

R$^1$, R$^2$ are each hydrogen, C$_{1-20}$-alkyl, C$_{3-12}$-cycloalkyl, aryl, C$_{7-20}$-aralkyl and C$_{7-20}$-alkylaryl or together represent (CH$_2$)$_j$-X-(CH$_2$)$_k$, R$^3$, R$^4$ are each hydrogen, alkyl such as C$_{1-200}$-alkyl, cycloalkyl such as C$_{3-12}$-cycloalkyl, hydroxyalkyl such as C$_{1-20}$-hydroxyalkyl, aminoalkyl such as C$_{1-20}$-aminoalkyl, hydroxyalkylaminoalkyl such as C$_{1-20}$- hydroxyalkylaminoalkyl, alkoxyalkyl such as C$_{2-30}$-alkoxyalkyl, dialkylaminoalkyl such as C$_{3-30}$-dialkylaminoalkyl, alkylaminoalkyl such as C$_{2-30}$-alkylaminoalkyl, R$^5$—(OCR$^6$R$^7$CR$^8$R$^9$)$_n$—(OCR$^6$R$^7$), aryl, heteroaryl, aralkyl such as C$_{7-20}$-aralkyl, heteroarylalkyl such as C$_{4-20}$-heteroarylalkyl, alkylaryl such as C$_{7-20}$-alkylaryl, alkylheteroaryl such as C$_{4-20}$-alkylheteroaryl and Y—(CH$_2$)$_m$-NR$^5$—(CH$_2$)$_q$ or together represent (CH$_2$)$_l$—X—(CH$_2$)$_m$ or R$^2$ and R$^4$ together represent (CH$_2$)$_l$—X—(CH$_2$)$_m$, R$^5$, R$^{10}$ are each hydrogen, C$_{1-4}$-alkyl, C$_{7-40}$-alkylphenyl, R$^6$, R$^7$, R$^8$, R$^9$ are each hydrogen, methyl or ethyl, X is CH$_2$, CHR$^5$, oxygen (O), sulfur (S) or NR$^5$, Y is N(R$^{10}$)$_2$, hydroxy, C$_{2-20}$-alkylaminoalkyl or C$_{3-20}$-dialkylaminoalkyl, n is an integer from 1 to 30 and j, k, l, m, q are each an integer from 1 to 4, are of particular economic importance.

The process of the present invention is therefore preferably employed for preparing the amines I by reacting primary or secondary alcohols of the formula II

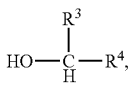

or aldehydes or ketones of the formula VI or VII

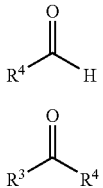

with nitrogen compounds of the formula III

where $R^1$, $R^2$, $R^3$ and $R^4$ are as defined above.

As can be seen from the definitions of the radicals $R^2$ and $R^4$, the reaction can also occur intramolecularly in an appropriate amino alcohol, amino ketone or amino aldehyde.

To prepare the amine I, a hydrogen atom of the amine III is, purely formally, replaced by the alkyl radical $R^4(R^3)$CH— with liberation of one molar equivalent of water.

The process of the present invention is also preferably employed in the preparation of cyclic amines of the formula IV

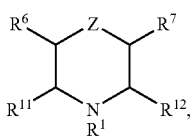

where
$R^{11}$ and $R^{12}$ are each hydrogen, $C_1$–$C_{20}$-alkyl, $C_3$–$C_{12}$-cycloalkyl, aryl, heteroaryl, $C_7$–$C_{20}$-aralkyl and $C_7$–$C_{20}$-alkylaryl,
Z is $CH_2$, $CHR^5$, O, $NR^5$ or $NCH_2CH_2OH$ and
$R^1$, $R^6$, $R^7$ are as defined above,
by reacting alcohols of the formula V

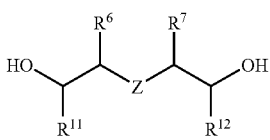

with ammonia or primary amines of the formula VI

 $R^1$—$NH_2$ (VI).

The substituents $R^1$ to $R^{12}$, the variables X, Y, Z and the indices j, k, l, m, n and q in the compounds I, II, III, IV, V and VI have, independently of one another, the following meanings:

$R^1$, $R^2$, $R^3$, $R^4$, $R^5$, $R^6$, $R^7$, $R^8$, $R^9$, $R^{10}$, $R^{11}$, $R^{12}$:
  hydrogen (H),
$R^3$, $R^4$:
  $C_{1-200}$-alkyl, preferably $C_{1-14}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, cyclohexylmethyl, n-octyl, isooctyl, 2-ethylhexyl, n-decyl, 2-n-propyl-n-heptyl, n-tridecyl, 2-n-butyl-n-nonyl and 3-n-butyl-n-nonyl, particularly preferably isopropyl, 2-ethylhexyl, n-decyl, 2-n-propyl-n-heptyl, n-tridecyl, 2-n-butyl-n-nonyl and 3-n-butyl-n-nonyl, and also preferably $C_{40-200}$-alkyl such as polybutyl, polyisobutyl, polypropyl, polyisopropyl and polyethyl, particularly preferably polybutyl and polyisobutyl,
  $C_{1-20}$-hydroxyalkyl, preferably $C_{1-8}$-hydroxyalkyl, particularly preferably $C_{1-4}$-hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl,
  $C_{1-20}$-aminoalkyl, preferably $C_{1-8}$-aminoalkyl such as aminomethyl, 2-aminoethyl, 2-amino-1,1-dimethylethyl, 2-amino-n-propyl, 3-amino-n-propyl, 4-amino-n-butyl, 5-amino-n-pentyl, N-(aminoethyl)aminoethyl and N-(aminoethyl)aminomethyl,
  $C_{2-20}$-hydroxyalkylaminoalkyl, preferably $C_{3-8}$-hydroxyalkyl-aminoalkyl such as (2-hydroxyethylamino)methyl, 2-(2-hydroxy-ethylamino)ethyl and 3-(2-hydroxyethylamino)propyl,
  $C_{2-30}$-alkoxyalkyl, preferably $C_{2-20}$-alkoxyalkyl, particularly preferably $C_{2-8}$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, particularly preferably $C_2$–$C_4$-alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl,
  $R^5$—$(OCR^6R^7CR^8R^9)n$-$(OCR^6R^7)$, preferably $R^5$—$(OCHR^7CHR^9)n$—$(OCR^6R^7)$ particularly preferably $R^5$—$(OCH_2CHR^9)_n$—$(OCR^6R^7)$,
  $C_{3-30}$-dialkylaminoalkyl, preferably $C_{3-20}$-dialkylaminoalkyl, particularly preferably $C_{3-10}$-N,N-dialkylaminoalkyl such as N,N-dimethylaminomethyl, 2-(N,N-dibutylamino)methyl, 2-(N,N-dimethylamino)ethyl, 2-(N,N-diethylamino)ethyl, 2-(N,N-dibutylamino)ethyl, 2-(N,N-di-n-propylamino) ethyl and 2-(N,N-diisopropylamino)ethyl, $(R^5)_2N$—$(CH_2)_q$,
  $C_{2-30}$-alkylaminoalkyl, preferably $C_{2-20}$-alkylaminoalkyl, particularly preferably $C_{2-8}$-alkylaminoalkyl such as methylaminomethyl, methylaminoethyl, ethylaminomethyl, ethylaminoethyl and isopropylaminoethyl, $(R^5)$HN—$(CH_2)_q$,
  Y—$(CH_2)_m$—$NR^5$—$(CH_2)$ q,
  $C_{4-20}$-heteroarylalkyl such as pyrid-2-ylmethyl, furan-2-ylmethyl, pyrrol-3-ylmethyl and imidazol-2-ylmethyl,
  $C_{4-20}$-alkylheteroaryl such as 2-methyl-3-pyridinyl, 4,5-dimethylimidazol-2-yl, 3-methyl-2-furanyl and 5-methyl-2-pyrazinyl,
  heteroaryl such as 2-pyridinyl, 3-pyridinyl, 4-pyridinyl, pyrazinyl, pyrrol-3-yl, imidazol-2-yl, 2-furanyl and 3-furanyl,
$R^1$, $R^2$, $R^3$, $R^4$:
  $C_{3-12}$-cycloalkyl, preferably $C_{3-8}$-cycloalkyl such as cyclopropyl, cyclobutyl, cyclopentyl, cyclohexyl, cycloheptyl and cyclooctyl, particularly preferably cyclopentyl, cyclohexyl and cyclooctyl, aryl such as phenyl, 1-naphthyl, 2-naphthyl, 1-anthryl, 2-anthryl and 9-anthryl, preferably phenyl, 1-naphthyl and 2-naphthyl, particularly preferably phenyl, $C_{7-20}$-alkylaryl, preferably $C_{7-12}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_{7-20}$-aralkyl, preferably $C_{7-12}$-phenylalkyl such as benzyl, p-methoxybenzyl, 3,4-dimethoxybenzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl, particularly preferably benzyl, 1-phenethyl and 2-phenethyl, $R^3$ and $R^4$ or $R^2$ and $R^4$ together represent a $-(CH_2)_l-X-(CH_2)_m-$ group such as $-(CH_2)_3-$, $-(CH_2)_4-$, $-(CH_2)_5-$, $-(CH_2)_6-$, $-(CH_2)_7-$, $-(CH_2)-O-(CH_2)_2-$, $-(CH_2)-NR^5-(CH_2)_2-$, $-(CH_2)_2-O-(CH_2)_2-NR^5-(CH_2)_2-$, $-CH_2-O-(CH_2)_3-$, $-CH_2-NR^5-(CH_2)_3-$, $R^1$, $R^2$:

$C_{1-20}$-alkyl, preferably $C_{1-8}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, particularly preferably $C_{1-4}$-alkyl such as methyl, ethyl, n-propyl, isopropyl, n-butyl, isobutyl, sec-butyl and tert-butyl, $R^1$ and $R^2$ together represent $-(CH_2)_j-X-(CH_2)_k-$ group such as $-(CH_2)_3-$, $-(CH_2)_4-$, $-(CH_2)_5-$, $-(CH_2)_6-$, $-(CH_2)_7-(CH_2)-O-(CH_2)_2-$, $-(CH_2)-NR^5-(CH_2)_2-$, $-(CH_2)_2-O-(CH_2)_2-NR^5-(CH_2)_2-$, $-CH_2-O-(CH_2)_3-$, $-CH_2-NR^5-(CH_2)_3-$, $R^5$, $R^{10}$:

$C_{1-4}$-alkyl such as methyl, ethyl, n-propyl, isopropyl, n-butyl, isobutyl, sec-butyl and tert-butyl, preferably methyl and ethyl, particularly preferably methyl, $C_{7-40}$-alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2-, 3-, 4-nonylphenyl, 2-, 3-, 4-decylphenyl, 2,3-, 2,4-, 2,5-, 3,4-, 3,5-dinonylphenyl, 2,3-, 2,4-, 2,5-, 3,4- and 3,5-didecylphenyl, $R^6$, $R^7$, $R^8$, $R^9$:

methyl or ethyl, preferably methyl, $R^{11}$, $R^{12}$:

$C_1$–$C_{20}$-alkyl, $C_3$–$C_{12}$-cycloalkyl, aryl, heteroaryl, $C_7$–$C_{20}$-aralkyl and $C_7$–$C_{20}$-alkylaryl, in each case as defined above,

X:

$CH_2$, $CHR^5$, oxygen (O), sulfur (S) or $NR^5$, preferably $CH_2$ and O,

Y:

$N(R^{10})_2$, preferably $NH_2$ and $N(CH_3)_2$, hydroxy (OH), $C_{2-20}$-alkylaminoalkyl, preferably $C_{2-16}$-alkylaminoalkyl such as methylaminomethyl, methylaminoethyl, ethylaminomethyl, ethylaminoethyl and isopropylaminoethyl, $C_{3-20}$-dialkylaminoalkyl, preferably $C_{3-16}$-dialkylaminoalkyl, such as dimethylaminomethyl, dimethylaminoethyl, diethylaminoethyl, di-n-propylaminoethyl and di-isopropylaminoethyl,

Z:

$CH_2$, $CHR^5$, O, $NR^5$ or $NCH_2CH_2OH$, j, l:

an integer from 1 to 4, e.g. 1, 2, 3 and 4, preferably 2 and 3, particularly preferably 2, k, m, q:

an integer from 1 to 4, e.g. 1, 2, 3 and 4, preferably 2, 3 and 4, particularly preferably 2 and 3, n:

an integer from 1 to 10, preferably an integer from 1 to 8, e.g. 1, 2, 3, 4, 5, 6, 7 or 8, particularly preferably an integer from 1 to 6.

Virtually all primary and secondary alcohols having an aliphatic OH function are suitable as alcohols. The alcohols can be linear, branched or cyclic. Secondary alcohols are aminated just like primary alcohols. As regards the number of carbon atoms in the alcohols which can be aminated, there are virtually no restrictions. The alcohols can also bear substituents which are inert under the conditions of the hydrogenative amination, for example alkoxy, alkenyloxy, alkylamino or dialkylamino groups. If polyhydric alcohols are to be aminated, controlling the reaction conditions makes it possible to obtain amino alcohols, cyclic amines or multiply aminated-products.

The amination of 1,4-diols leads, depending on the reaction conditions selected, to 1-amino-4-hydroxy or 1,4-diamino compounds or to five-membered rings containing a nitrogen atom (pyrrolidines).

The amination of 1,6-diols leads, depending on the reaction conditions selected, to 1-amino-6-hydroxy or 1,6-diamino compounds or to seven-membered rings containing a nitrogen atom (hexamethylenimines).

The amination of 1,5-diols leads, depending on the reaction conditions selected, to 1-amino-5-hydroxy or 1,5-diamino compounds or to six-membered rings containing a nitrogen atom (piperidines). Accordingly, amination of diglycol by means of $NH_3$ can give monoaminodiglycol (=ADG=$H_2N-CH_2CH_2-O-CH_2CH_2-OH$), diaminodiglycol or, particularly preferably, morpholine. Similarly, diethanolamine particularly preferably gives piperazine. N-(2-Hydroxyethyl)piperazine can be obtained from triethanolamine.

Preference is given, for example, to aminating the following alcohols:

ethanol, ethanol, n-propanol, isopropanol, n-butanol, isobutanol, n-pentanol, n-hexanol, 2-ethylhexanol, tridecanol, stearyl alcohol, palmityl alcohol, cyclobutanol, cyclopentanol, cyclohexanol, benzyl alcohol, 2-phenylethanol, 2-(p-methoxyphenyl)ethanol, 2-(3,4-dimethoxyphenyl) ethanol, 1-phenyl-3-butanol, ethanolamine, n-propanolamine, isopropanolamine, 2-amino-1-propanol, 1-methoxy-2-propanol, 3-amino-2,2-dimethyl-1-propanol, n-pentanolamine (1-amino-5-pentanol), n-hexanolamine (1-amino-6-hexanol), ethanolamine, diethanolamine, triethanolamine, N-alkyldiethanolamines, diisopropanolamine, 3-(2-hydroxyethylamino)propan-1-ol, 2-(N,N-dimethylamino)ethanol, 2-(N,N-diethylamino)ethanol, 2-(N,N-di-n-propylamino)ethanol, 2-(N,N-diisopropylamino) ethanol, 2-(N,N-di-n-butylamino)ethanol, 2-(N,N-diisobutylamino)ethanol, 2-(N,N-di-sec-butylamino) ethanol, 2-(N,N-di-tert-butylamino)ethanol, 3-(N,N-dimethylamino)propanol, 3-(N,N-diethylamino)propanol, 3-(N,N-di-n-propylamino)propanol, 3-(N,N-diisopropylamino)propanol, 3-(N,N-di-n-butylamino)propanol, 3-(N,N-diisobutylamino)propanol, 3-(N,N-di-sec-butylamino)propanol, 3-(N,N-di-tert-butylamino)propanol, 1-dimethylamino-4-pentanol, 1-diethylamino-4-pentanol, ethylene glycol, 1,2-propylene glycol, 1,3-propylene glycol, diglycol, 1,4-butanediol, 1,5-pentanediol, 1,6-hexanediol, 2,2-bis[4-hydroxycyclohexyl]propane, methoxyethanol, propoxyethanol, butoxyethanol, polyisobutyl alcohols, polypropyl alcohols, polyethylene glycol ethers, polypropylene glycol ethers and polybutylene glycol ethers. The latter polyalkylene glycol ethers are converted into the corresponding amines in the reaction of the present invention by transformation of their free hydroxyl groups.

Particularly preferred alcohols are methanol, ethanol, n-propanol, i-propanol, n-butanol, sec-butanol, tert-butanol, fatty alcohols, ethylene glycol, diethylene glycol, 2-(2-dimethylaminoethoxy)ethanol, N-methyldiethanolamine and 2-(2-dimethylaminoethoxy)ethanol.

Ketones which are suitable for use in the process of the present invention include virtually all aliphatic and aromatic ketones. The aliphatic ketones can be linear, branched or cyclic and the ketones can contain heteroatoms. As regards the number of carbon atoms in the aminatable ketones, there are virtually no restrictions. The ketones can also bear substituents which are inert under the conditions of the hydrogenative amination, for example alkoxy, alkenyloxy, alkylamino or dialkylamino groups. If polyfunctional ketones are to be aminated, controlling the reaction conditions makes it possible to obtain amino ketones, amino alcohols, cyclic amines or multiply aminated products.

Preference is given, for example, to aminatively hydrogenating the following ketones:
acetone, ethyl methyl ketone, methyl vinyl ketone, isobutyl methyl ketone, 3-methylbutan-2-one, diethyl ketone, tetralone, acetophenone, p-methylacetophenone, p-methoxyacetophenone, m-methoxyacetophenone, 1-acetylnaphthalene, 2-acetylnaphthalene, 1-phenyl-3-butanone, cyclobutanone, cyclopentanone, cyclopentenone, cyclohexanone, cyclohexenone, 2,6-dimethylcyclohexanone, cycloheptanone, cyclododecanone, acetylacetone, methylglyoxal and benzophenone.

Aldehydes which are suitable for use in the process of the present invention include virtually all aliphatic and aromatic aldehydes. The aliphatic aldehydes can be linear, branched or cyclic, and the aldehydes can contain heteroatoms. As regards the number of carbon atoms in the aminatable aldehydes, there are virtually no restrictions. The aldehydes can also bear substituents which are inert under the conditions of the hydrogenative amination, for example alkoxy, alkenyloxy, alkylamino or dialkylamino groups. If polyfunctional aldehydes or ketoaldehydes are to be aminated, controlling the reaction conditions makes it possible to obtain amino alcohols, cyclic amines or multiply aminated products.

Preference is given, for example, to aminatively hydrogenating the following aldehydes:
formaldehyde, acetaldehyde, propionaldehyde, n-butyraldehyde, isobutyraldehyde, pivalaldehyde, n-pentanal, n-hexanal, 2-ethylhexanali 2-methylpentanal, 3-methylpentanal, 4-methylpentanal, glyoxal, benzaldehyde, p-methoxybenzaldehyde, p-methylbenzaldehyde, phenylacetaldehyde, (p-methoxyphenyl)acetaldehyde, (3,4-dimethoxyphenyl)acetaldehyde, 4-formyltetrahydropyran, 3-formyltetrahydrofuran, 5-formylvaleronitrile, citronellal, acrolein, methacrolein, ethylacrolein, citral, crotonaldehyde, 3-methoxypropionaldehyde, 3-amino-propionaldehyde, hydroxypivalaldehyde, dimethylolpropionaldehyde, dimethylolbutyraldehyde, furfural, glyoxal, glutaraldehyde and also hydroformylated oligomers and polymers, e.g. hydroformylated polyisobutene (polyisobutenaldehyde) or the oligomer obtained by metathesis of 1-pentene and cyclopentene and subsequent hydroformylation.

As aminating agent in the hydrogenative amination of alcohols, aldehydes or ketones in the presence of hydrogen, it is possible to use either ammonia or primary or secondary, aliphatic or cycloaliphatic or aromatic amines.

When ammonia is used as aminating agent, the alcoholic hydroxyl group or the aldehyde group or the keto group is firstly converted into the primary amino group ($-NH_2$). The primary amine formed in this way can react with further alcohol or aldehyde or ketone to form the corresponding secondary amine and this can in turn react with further alcohol or aldehyde or ketone to form the corresponding, preferably symmetrical tertiary amine. Depending on the composition of the reaction mixture or the feed stream (in the case of the continuous process) and depending on the reaction conditions employed, viz. pressure, temperature, reaction time (space velocity over the catalyst), primary, secondary or tertiary amines can be prepared preferentially as desired in this way.

Cyclic amines such as pyrrolidines, piperidines, hexamethylenimines, piperazines and morpholines can be prepared in this way from polyhydric alcohols or dialdehydes or oligoaldehydes or diketones or oligoketones or ketoaldehydes by intramolecular hydrogenative amination.

Primary or secondary amines can also be used as aminating agents just like ammonia.

These aminating agents are preferably used for preparing unsymmetrically substituted dialkylamines or trialkylamines, e.g. ethyldiisopropylamine and ethyldicyclohexylamine. For example, the following monoalkylamines and dialkylamines are used as aminating agents: methylamine, dimethylamine, ethylamine, diethylamine, n-propylamine, di-n-propylamine, isopropylamine, diisopropylamine, isopropylethylamine, n-butylamine, di-n-butylamine, s-butylamine, di-s-butylamine, isobutylamine, n-pentylamine, s-pentylamine, isopentylamine, n-hexylamine, s-hexylamine, isohexylamine, cyclohexylamine, aniline, toluidine, piperidine, morpholine and pyrrolidine.

The aminating agent can be used in stoichiometric, substoichiometric or superstoichiometric amounts based on the alcoholic hydroxyl group or aldehyde group or keto group to be aminated.

In the case of the amination of alcohols, aldehydes or ketones using primary or secondary amines, the amine is preferably used in an approximately stoichiometric amount or slightly superstoichiometric amount per mole of alcoholic hydroxyl group, aldehyde group or keto group to be aminated.

Ammonia is generally used in an amount of from 1.5 to 250 mol, preferably from 2 to 100 mol, in particular from 2 to 10 mol, per mole of alcoholic hydroxyl group, aldehyde group or keto group to be reacted.

Larger excesses both of ammonia and of primary or secondary amines are possible.

The process of the present invention can be carried out batchwise or preferably continuously as follows, with the catalyst preferably being arranged as a fixed bed in the reactor.

However, it can also be carried out as a fluidized-bed reaction with upward and downward turbulent motion of the catalyst material.

The amination of the primary or secondary alcohol groups, aldehyde groups or ketone groups of the starting material can be carried out in the liquid phase or in the gas phase. Preference is given to a fixed-bed process in the gas phase.

When the reaction is carried out in the liquid phase, the starting materials (alcohol, aldehyde or ketone plus ammonia or amine) are simultaneously passed in liquid form at pressures of generally from 5 to 30 MPa (50–300 bar), preferably from 5 to MPa, particularly preferably from 15 to 25 MPa, and temperatures of generally from 80 to 300° C., preferably from 120 to 270° C., particularly preferably from 130 to 250° C., in particular from 170 to 230° C., including hydrogen over the catalyst which is usually located in a fixed-bed reactor which is preferably heated from the outside. Operation in the downflow mode or in the upflow mode is possible. The space velocity over the catalyst is generally in the range from 0.05 to 5 kg, preferably from 0.1 to 2 kg, particularly preferably from 0.2 to 0.6 kg, of alcohol, aldehyde or ketone per liter of catalyst (bed volume) and hour. If desired, the starting materials can be diluted with a suitable solvent such as tetrahydrofuran, dioxane, N-methylpyrrolidone or ethylene glycol dimethyl ether. It is advantageous to preheat the reactants before they are introduced into the reaction vessel, preferably to the reaction temperature.

When the reaction is carried out in the gas phase, the gaseous starting materials (alcohol, aldehyde or ketone plus ammonia or amine) in a gas stream, preferably hydrogen, sufficiently large to achieve vaporization are passed at pressures of generally from 0.1 to 40 MPa (1 to 400 bar), preferably from 0.1 to 10 MPa, particularly preferably from 0.1 to 5 MPa, in the presence of hydrogen over the catalyst. The temperatures for the amination of alcohols are generally from 80 to 300° C., preferably from 120 to 270° C., particularly preferably from 160 to 250° C. The reaction temperatures in the hydrogenative amination of aldehydes and ketones are generally from 80 to 300° C., preferably from 100 to 250° C. The reaction mixture can be passed through the catalyst bed from the top downward or from the bottom upward. The gas stream required is preferably obtained by means of circulating gas operation.

The space velocity of the catalyst is generally in the range from 0.01 to 2 kg, preferably 0.05 to 0.5 kg, of alcohol, aldehyde or ketone per liter of catalyst (bed volume) and hour.

The hydrogen is generally fed to the reaction in an amount of from 5 to 400 l, preferably from 50 to 200 l, per mole of alcohol, aldehyde or ketone component, with the liter figures in each case being based on standard-conditions (S.T.P.).

The amination of aldehydes or ketones is different from the amination of alcohols in that at least stoichiometric amounts of hydrogen have to be present in the amination of aldehydes and ketones.

Both when the reaction is carried out in the liquid phase and when it is carried out in the gas phase, it is possible to employ elevated temperatures and elevated total pressures. The pressure in the reaction vessel resulting from the sum of the partial pressures of the aminating agent, the alcohol, aldehyde or ketone and the reaction products formed and any solvent used at the indicated temperatures is advantageously increased to the desired reaction pressure by injection of hydrogen.

Both when the reaction is carried out continuously in the liquid phase and when it is carried out continuously in the gas phase, the excess aminating agent can be circulated together with the hydrogen.

If the catalyst is present as a fixed bed, it can be advantageous in terms of the selectivity of the reaction to mix the shaped catalyst bodies with inert bodies in the reactor so as to "dilute" them. The proportion of inert bodies in such catalyst preparations can be from 20 to 80 parts by volume, preferably from 30 to 60 parts by volume and in particular from 40 to 50 parts by volume.

The water of reaction formed during the course of the reaction (in each case one mol per mole of alcohol group, aldehyde group or ketone group reacted) generally does not have an adverse effect on the conversion, the reaction rate, the selectivity and the operating life of the catalyst and is therefore advantageously removed from the reaction product only during the work-up of the latter, e.g. by distillation.

The crude reaction mixture after the reaction is advantageously depressurized and the excess aminating agent and the hydrogen are then removed and the amination products obtained are purified by distillation or rectification, liquid extraction or crystallization. The excess aminating agent and the hydrogen are advantageously recirculated to the reaction zone. The same applies to any incompletely reacted alcohol, aldehyde or ketone component.

The amines which are obtainable according to the present invention are suitable, inter alia, as intermediates in the preparation of fuel additives (U.S. Pat. No. 3,275,554; DE-A-21 25 039 and DE-A-36 11 230), surfactants, drugs and crop protection agents and also of vulcanization accelerators.

EXAMPLES

A) Preparation of Zirconium-Copper-Nickel-Cobalt Catalysts having Sodium Contents of from 0.11 to 1.1% by Weight, Calculated as Sodium Oxide To carry out the precipitation, a constant stream of an aqueous solution of nickel nitrate, copper nitrate, cobalt nitrate and zirconium acetate was introduced simultaneously with a 20% strength aqueous sodium carbonate solution into a stirred vessel at 70° C. so that the pH measured by means of a glass electrode was maintained in a range from 6.0 to 7.0. The concentration of the metal salts in the metal salt solution was set so that a catalyst having a calculated weight ratio of $NiO/CoO/CuO/ZrO_2$ of 1/1/0.393/1.179 finally resulted. After all the metal salt solution and sodium carbonate solution had been added, the mixture was stirred at 70° C. for another hour and the pH was subsequently increased to 7.4 by addition of a little sodium carbonate solution.

The suspension obtained was filtered and the filter cake was washed with deionized water. Different washing times, i.e. residence times of the washing water at the filter cake, or different amounts of washing water resulted in catalysts having different sodium contents. The filter cake was then dried at 200° C. in a drying oven or a spray dryer. The hydroxide/carbonate mixture obtained in this way was then heat treated at 400° C. for 2 hours.

The catalyst powders A1 to A5 obtained in this way had the compositions:

A1:

27.97% by weight of Ni, calculated as NiO, 27.97% by weight of Co, calculated as CoO, 10.99% by weight of Cu, calculated as CuO, 32.96% by weight of Zr, calculated as $ZrO_2$, 0.11% by weight of Na, calculated as $Na_2O$.

A2:
27.97% by weight of Ni, calculated as NiO,
27.97% by weight of Co, calculated as CoO,
10.98% by weight of Cu, calculated as CuO,
32.96% by weight of Zr, calculated as $ZrO_2$,
0.12% by weight of Na, calculated as $Na_2O$.

A3:
27.96% by weight of Ni, calculated as NiO,
27.96% by weight of Co, calculated as CoO,
10.99% by weight of Cu, calculated as CuO,
32.95% by weight of Zr, calculated as $ZrO_2$,
0.14% by weight of Na, calculated as $Na_2O$.

A4:
27.91% by weight of Ni, calculated as NiO,
27.91% by weight of Co, calculated as CoO,
10.97% by weight of Cu, calculated as CuO,
32.89% by weight of Zr, calculated as $ZrO_2$,
0.32% by weight of Na, calculated as $Na_2O$.

A5 (Not According to the Present Invention):
27.69% by weight of Ni, calculated as NiO,
27.69% by weight of Co, calculated as CoO,
10.88% by weight of Cu, calculated as CuO,
32.64% by weight of Zr, calculated as $ZrO_2$,
1.10% by weight of Na, calculated as $Na_2O$.

The alkali metal content was determined by means of atomic spectrometry. The lower analytical detection limit for alkali metals in this method was 0.01% by weight.

The catalyst powders were in each case mixed with 3% by weight of graphite and shaped to form 5×3 mm pellets.

Five different catalysts A1 to A5 whose catalytically active compositions had Na contents ranging from 0.11% by weight to 1.1% by weight, in each case calculated as sodium oxide ($Na_2O$) were prepared in this way.

After tableting, the pellets were in each case calcined at 400° C. for 2 hours in a muffle furnace.

Before the respective catalyst was installed in the test reactor, it was reduced and subsequently passivated:

To reduce the catalyst, it was heated to from 100 to 200° C. in a stream of hydrogen/nitrogen. This temperature was maintained until all evolution of heat due to the exothermic reduction in the reduction furnace and monitored by means of thermocouples along the furnace tube had ceased. The catalyst was subsequently heated to a final temperature of 280° C. and this temperature was held for 6 hours. The catalyst was cooled to room temperature in a stream of nitrogen and then passivated using a dilute oxygen stream. In the passivation, it was ensured that the temperature did not exceed 50° C. at any point in the reactor.

B) Hydrogenated Aminations Using Catalysts Prepared in A)

Example 1

Preparation of Morpholine by Hydrogenative Amination of Diglycol

General Procedure:
100 cm³ of catalyst A were installed in a continuously operated high-pressure reactor (upflow mode). After the reactor had been closed, 20 standard l/h (standard l=standard liters=volume at S.T.P.) of hydrogen were passed over the catalyst. The pressure was set to 50 bar. The temperature was subsequently increased to 180° C. at 2° C./minute. The pressure was then adjusted to 200 bar. Finally, diethylene glycol (60 g/h, 0.57 mol/h) and ammonia (60 g/h, 3.53 mol/h) were fed in (WHSV: 0.6 kg of diethylene glycol/ [$l_{catalyst}$·h]). The reaction temperature was initially maintained at 200° C. for 16 hours. During this time, the catalyst was fully activated. The reaction temperature was subsequently reduced to 180° C. After the output from the reactor had been depressurized, excess ammonia was distilled off.

Analysis: GC analysis in percent by area. Samples diluted with water in a ratio of 1:10. 30 m of RTX-5 amines, 0.32 mm, 1.5 µm, temperature program: 80° C./4 min., then at 10° C./min. to 280° C., then 280° C./5 min.

The catalysts A1 to A5 with different sodium contents were used in this general procedure.

The results are shown in FIGS. 1 and 2 below.

It can be seen that the conversion and thus the catalyst productivity achieved at a reaction temperature of 180° C. increases significantly with decreasing Na content of the catalysts A5 to A1 (FIG. 1). The catalysts thus become more active with decreasing Na content.

Furthermore, the (conversion dependent) selectivity to undesirable decarbonylation (indicators: 2-methoxyethanol and 2-methoxyethylamine) drops with decreasing Na content (FIG. 2).

Example 2

Preparation of Morpholine by Hydrogenative Amination of Diglycol

Using the general experimental procedure of example 1, the two catalysts A2 and A5 were compared at the same diglycol conversion. For this purpose, a reaction temperature of 190° C. was employed for the catalyst A2 (Na content: 0.12%). To achieve the same conversion (based on diethylene glycol), a reaction temperature of 200° C. had to be employed for the catalyst A5 (Na content: 1.10%).

The results are shown in the following table.

Catalyst A2 displayed a higher total selectivity to the two desired products (morpholine and aminodiglycol). The formation of methoxyethanol and methoxyethylamine, each indicators of undesirable secondary reactions, was a factor of 4 lower in the case of catalyst A2 than in the case of catalyst A5.

| Catalyst | T °C. | Conversion % | S (MOR) % | S (ADG) % | S (MOR + ADG) % | EtNH2 | MeOEtOH | MeOEtNH2 | Na content % by weight |
|---|---|---|---|---|---|---|---|---|---|
| A2 | 190 | 93.2 | 77.7 | 9.89 | 87.6 | 0.1 | 0.07 | 0.08 | 0.12 |
| A5 | 200 | 92.9 | 80.15 | 6.64 | 86.8 | 0.14 | 0.3 | 0.28 | 1.10 |

S=selectivity (based on diglycol reacted)
MOR=morpholine
ADG=aminodiglycol ($H_2N(CH_2)_2O(CH_2)_2OH$)
MeOEtOH=2-methoxyethanol
MeOEtNH2=2-methoxyethylamine Example 3

Amination of Hydroformylated Polyisobutene

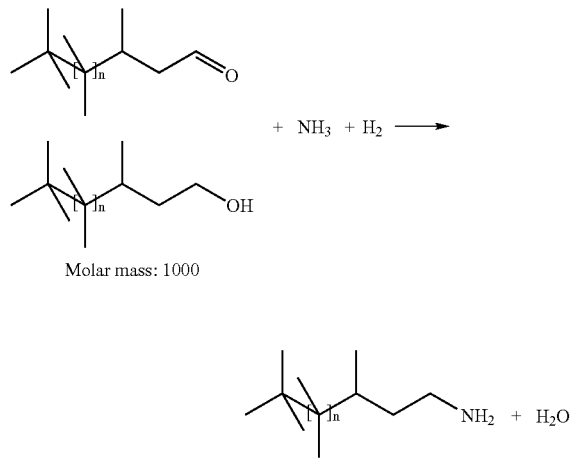

Molar mass: 1000

The experiments were carried out using a catalyst having the composition 28.0% by weight of Ni, calculated as NiO,
28.0% by weight of Co, calculated as CoO,
11.0% by weight of Cu, calculated as CuO,
32.99% by weight of Zr, calculated as $ZrO_2$,
0.01% by weight of Na, calculated as $Na_2O$, which had been prepared in a manner analogous to the procedure described above in example A, in a 1 m³ tube reactor (upflow mode). The catalyst was installed in reduced/passivated form.

The reactor was firstly flushed 3 times with 40 bar of $N_2$. After testing for the absence of leaks at 200 bar of $N_2$, the reactor was depressurized to 120 bar. The circulating gas compressor was started up at a flow rate of 1000 standard m³/h of $N_2$ and the introduction of ammonia was commenced at ambient temperature. At a temperature of about 120° C., the ammonia feed was switched off briefly, resulting in a further temperature rise to a maximum of 183° C. being observed. After cooling, the amount of ammonia was increased stepwise to the target value for the synthesis of 250 kg/h and the reactor was heated to 190° C. While introducing ammonia, the introduction of $H_2$ was commenced and a pressure of 200 bar was established. The following parameters were set.

| Pressure (bar) | Temp. (° C.) | WHSV over cat. (kg/(l · h)) | Ammonia (kg/h) | Amount of circulating gas (standard m³/h) |
|---|---|---|---|---|
| 200 | 200 | 0.5–1.2 | 1500 | 1500 |
| 200 | 180 | 0.5–0.9 | 250 | 300 |

The results are shown in the following table.

| Running time (h) | T (° C.) | Feed (kg/h) | Ammonia (kg/h) | Circulating gas (standard m³/h) | AN (mg KOH/g) | AC (mg KOH/g) | s + t AN (mg KOH/g) |
|---|---|---|---|---|---|---|---|
| 21 | 176 | 250 | 250 | 1200 | 16.4 | 17.0 | 5.8 |
| 45 | 180 | 500 | 250 | 300 | 20.6 | 20.6 | 2.1 |
| 69 | 180 | 600 | 250 | 300 | 21.0 | 21.0 | 1.8 |
| 93 | 180 | 700 | 250 | 300 | 21.0 | 21.5 | 1.6 |
| 141 | 180 | 800 | 250 | 300 | 21.5 | 21.8 | 1.5 |
| 165 | 180 | 900 | 250 | 300 | 21.4 | 21.9 | 1.1 |
| 189 | 177 | 900 | 250 | 300 | 21.6 | 22.1 | 1.1 |
| 213 | 176 | 900 | 250 | 300 | 21.4 | 22.0 | 0.9 |
| 237 | 178 | 800 | 250 | 300 | 21.5 | 21.8 | 1.2 |
| 333 | 176 | 800 | 250 | 300 | 21.6 | 22.5 | 1.0 |
| 357 | 173 | 800 | 250 | 300 | 21.5 | 22.4 | 0.9 |
| 381 | 172 | 700 | 250 | 300 | 21.4 | 22.0 | 1.0 |
| 405 | 170 | 700 | 250 | 300 | 21.1 | 21.9 | 0.8 |
| 453 | 171 | 700 | 250 | 300 | 21.5 | 22.2 | 0.9 |
| 477 | 169 | 600 | 250 | 300 | 21.5 | 22.0 | 0.9 |
| 525 | 168 | 300 | 250 | 300 | 20.9 | 21.2 | 1.6 |

Explanation of the Abbreviations:

WHSV over cat.=space velocity (WHSV) over the catalyst in kg of (alcohol+aldehyde) per liter of catalyst and per hour.

standard m³=standard cubic meters=volume at S.T.P.

s+t AN is amine number based on alkylated secondary and tertiary amines.

(The AN is determined by a known method using an acid-based titration. Specifically, the base is titrated with HCl). The AN serves as a measure of the degree of amination.

AC is the acetylation number.

(To determine the AC, the sample is reacted with an acetylation mixture consisting of acetic anhydride (AA), glacial acetic acid and pyridine at room temperature according to a known method.

In the present cases, the base reacts with AA to form the amide. Excess AA is converted by means of $H_2O$ into acetic acid which is in turn backtitrated with NaOH.

The AC determined serves as a measure of the total potential of functional groups of the product. Together with the AN it indicates the corresponding amine fraction.

We claim:

1. A process for preparing amines by reacting primary or secondary alcohols, aldehydes or ketones with hydrogen and nitrogen compounds selected from the group consisting of ammonia and primary and secondary amines at elevated temperature and superatmospheric pressure in the presence of a catalyst whose catalytically active composition prior to treatment with hydrogen comprises from 22 to 40% by weight of oxygen-containing compounds of zirconium, calculated as $ZrO_2$, from 1 to 30% by weight of oxygen-containing compounds of copper, calculated as CuO, from 15 to 50% by weight of oxygen-containing compounds of nickel, calculated as NiO, with the molar ratio of nickel to copper being greater than 1, from 15 to 50% by weight of oxygen-containing compounds of cobalt, calculated as CoO, and less than 0.5% by weight of alkali metal, calculated as alkali metal oxide.

2. A process as claimed in claim 1, wherein the catalytically active composition of the catalyst prior to treatment with hydrogen contains less than 0.35% by weight of alkali metal, calculated as alkali metal oxide.

3. A process as claimed in claim 1, wherein the catalytically active composition of the catalyst prior to treatment with hydrogen contains less than 0.2% by weight of alkali metal, calculated as alkali metal oxide.

4. A process as claimed in claim 1, wherein the catalytically active composition of the catalyst prior to treatment with hydrogen comprises from 25 to 40% by weight of oxygen-containing compounds of zirconium, calculated as $ZrO_2$, from 2 to 25% by weight of oxygen-containing compounds of copper, calculated as CuO, from 21 to 45% by weight of oxygen-containing compounds of nickel, calculated as NiO, with the molar ratio of nickel to copper being greater than 1, and from 21 to 45% by weight of oxygen-containing compounds of cobalt, calculated as CoO.

5. A process as claimed in claim 1, wherein the reaction is carried out at from 80 to 300° C.

6. A process as claimed in claim 1, wherein the reaction is carried out in the liquid phase at pressures of from 5 to 30 MPa or in the gas phase at pressures of from 0.1 to 40 MPa.

7. A process as claimed in claim 1 for preparing amines of the formula I

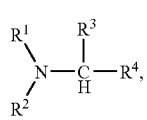

(I)

where $R^1$, $R^2$ are each hydrogen, $C_{1-20}$-alkyl, $C_{3-12}$-cycloalkyl, aryl, $C_{7-20}$aralkyl and $C_{7-20}$-alkylaryl or together represent $(CH_2)_j$—X—$(CH_2)_k$, $R_3$, $R_4$ are each hydrogen, alkyl, cycloalkyl, hydroxyalkyl, aminoalkyl, hydroxyalkylaminoalkyl, alkoxyalkyl, dialkylaminoalkyl, alkylaminoalkyl, $R^5$—$(OCR^6R^7CR^8R^9)_n$—$(OCR^6R^7)$, aryl, heteroaryl, aralkyl, heteroarylalkyl, alkylaryl, alkylheteroaryl and Y—$(CH_2)_m$—$NR^5$—$(CH_2)_q$ or together represent $(CH_2)_l$—X—$(CH_2)_m$ or $R^2$ and $R^4$ together represent $(CH_2)_l$—X—$(CH_2)_m$, $R^5$, $R^{10}$ are each hydrogen, $C_{1-4}$-alkyl, $C_{7-40}$-alkylphenyl, $R^6$, $R^7$, $R^8$, $R^9$ are each hydrogen, methyl or ethyl, X is $CH_2$, $CHR^5$, oxygen (O), sulfur (S) or NR5, Y is $N(R^{10})_2$, hydroxy, $C_{2-20}$-alkylaminoalkyl or $C_{3-20}$-dialkylaminoalkyl, n is an integer from 1 to 30 and j, k, l, m, q are each an integer from 1 to 4, by reacting primary or secondary alcohols of the formula II

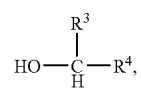

(II)

or aldehydes or ketones of the formula VI or VII

VI

VII with nitrogen compounds of the formula III

(III)

8. A catalyst whose catalytically active composition prior to treatment with hydrogen comprises from 22 to 40% by weight of oxygen-containing compounds of zirconium, calculated as $ZrO_2$, from 1 to 30% by weight of oxygencontaining compounds of copper, calculated as CuO, from 15 to 50% by weiaht of oxygen-containing compounds of nickel, calculated as NiO, with the molar ratio of nickel to copper being greater than 1, from 15 to 50% by weight of oxygen-containing compounds of cobalt, calculated as CoO, and less than 0.5% by weight of alkali metal, calculated as alkali metal oxide.

9. A process as claimed in claim 7 wherein, in the definition of $R^3$ and $R^4$, alkyl denotes $C_{1-200}$-alkyl, cycloalkyl denotes $C_{3-12}$-cycloalkyl, hydroxyalkyl denotes $C_{1-20}$-hydroxyalkyl, aminoalkyl denotes $C_{1-20}$-aminoalkyl, hydroxyalkylaminoalkyl denotes $C_{1-20}$-hydroxyalkylaminoalkyl, alkoxyalkyl denotes $C_{2-30}$-alkoxyalkyl, dialkylaminoalkyl denotes $C_{3-30}$-dialkylaminoalkyl, alkylaininoalkyl denotes $C_{2-30}$alkylaminoalkyl, aralkyl denotes $C_{7-20}$-aralkyl, heter-oarylalkyl denotes $C_{4-20}$-heteroarylalkyl, alkylaryl denotes $C_{7-20}$-alkylaryl, and alkyiheteroaryl denotes $C_{4-20}$-alkylheteroaryl.

* * * * *

UNITED STATES PATENT AND TRADEMARK OFFICE
CERTIFICATE OF CORRECTION

PATENT NO. : 7,183,438 B2  
APPLICATION NO. : 10/507602  
DATED : February 27, 2007  
INVENTOR(S) : Gerlach et al.

It is certified that error appears in the above-identified patent and that said Letters Patent is hereby corrected as shown below:

In Claim 7, column 20, indicated line 11:
"NR5" should read --$NR^5$--

In Claim 8, column 20, indicated line 45:
"oxygencontaining" should read --oxygen-containing--

In Claim 9, column 20, indicated lines 59 and 60:
"dial-kylaminoalkyl" should read --dialkylaminoalkyl--

In Claim 9, column 20, indicated lines 60 and 61:
"alkylaininoalkyl" should read --alkylaminoalkyl--

In Claim 9, column 20, indicated line 62:
"heter-oarylalkyl" should read --heteroarylalkyl--

In Claim 9, column 20, indicated line 63:
"alkyiheteroaryl" should read --alkylheteroaryl--

Signed and Sealed this

Tenth Day of July, 2007

JON W. DUDAS  
*Director of the United States Patent and Trademark Office*